United States Patent
Carson et al.

(10) Patent No.: US 7,827,853 B2
(45) Date of Patent: Nov. 9, 2010

(54) WELD TESTING APPARATUS AND METHOD FOR NOZZLES

(75) Inventors: Glenn Carson, Point Edward (CA); James Hodgins, Sarnia (CA)

(73) Assignee: CAR-BER Investments Inc., Point Edward (CA)

( * ) Notice: Subject to any disclaimer, the term of this patent is extended or adjusted under 35 U.S.C. 154(b) by 427 days.

(21) Appl. No.: 11/771,189

(22) Filed: Jun. 29, 2007

(65) Prior Publication Data

US 2007/0248202 A1    Oct. 25, 2007

Related U.S. Application Data

(63) Continuation of application No. PCT/CA2005/001982, filed on Dec. 30, 2005.

(60) Provisional application No. 60/663,871, filed on Mar. 22, 2005, provisional application No. 60/640,093, filed on Dec. 30, 2004.

(51) Int. Cl.
*G01M 3/04* (2006.01)
*G01M 3/08* (2006.01)
*F16L 55/10* (2006.01)

(52) U.S. Cl. .............. 73/49.8; 73/46; 138/90

(58) Field of Classification Search ........... 73/49.8, 73/49.2, 49.5, 46; 138/89–90
See application file for complete search history.

(56) References Cited

U.S. PATENT DOCUMENTS

| 5,024,079 | A | 6/1991 | Dufort |
| 5,056,680 | A * | 10/1991 | Sharp .................. 220/567.1 |
| 5,331,841 | A * | 7/1994 | Beaver et al. .............. 73/49.2 |
| 5,844,127 | A | 12/1998 | Berube et al. |
| 6,131,441 | A | 10/2000 | Berube et al. |
| 6,367,313 | B1 | 4/2002 | Lubyk |
| 6,463,791 | B1 | 10/2002 | Berube et al. |
| 6,675,634 | B2 | 1/2004 | Berneski, Jr. et al. |
| 6,729,797 | B2 * | 5/2004 | Manger et al. ............. 405/52 |
| 2003/0033855 | A1 * | 2/2003 | Manger et al. ............... 73/37 |
| 2003/0167827 | A1 * | 9/2003 | Berneski et al. .......... 73/49.8 |
| 2009/0084165 | A1 * | 4/2009 | Carson .................... 73/49.8 |

OTHER PUBLICATIONS

Written Opinion issued in the corresponding PCT Application No. PCT/CA2005/001982, dated Apr. 25, 2006.

* cited by examiner

*Primary Examiner*—Lisa M Caputo
*Assistant Examiner*—Jonathan Dunlap
(74) *Attorney, Agent, or Firm*—Santosh K. Chari; Blake, Cassels & Graydon LLP (57) ABSTRACT

A weld testing assembly for testing the integrity of weld used to secure a nozzle to a vessel and the like comprises a pair of plates or discs positioned on either end of the nozzle and a generally coaxially extending annular body having a diameter smaller than the nozzle stem. The assembly creates a sealed area with a small volume whereby a weld test can be efficiently conducted.

24 Claims, 10 Drawing Sheets

WELD TESTING APPARATUS AND METHOD FOR NOZZLES

CROSS REFERENCE TO PRIOR APPLICATIONS

This application is a Continuation of PCT Application No. PCT/CA2005/001982 filed on Dec. 30, 2005, which claims priority from U.S. Provisional application No. 60/640,093, filed Dec. 30, 2004 and U.S. Provisional application No. 60/663,871, filed Mar. 22, 2005. The disclosures of the aforementioned related applications are incorporated herein by reference in their entirety.

BACKGROUND OF THE INVENTION

1. Field of the Invention

The present invention relates to apparatus and methods for testing welds and, more particularly, for testing welds on nozzles or other such fixtures.

2. Description of the Prior Art

In chemical or petrochemical plants etc., it is often necessary to convey fluidic materials from one location, or holding cell to another. The conveyance of such material normally includes equipment such as conduits or pipes, storage or reaction vessels etc., which are generally manufactured from metal. The joining of separate pieces of the conveying equipment is generally achieved by welding the necessary pieces together. For example, when joining adjacent ends of pipe together, it is common for each end to be provided with flanges, welded to each respective end, which are then bolted together to form a seal. Alternatively, the ends of pipes or other equipment may be welded directly together for form the necessary conduit. In either case, it will be appreciated that each welded joint must form a complete seal so as to prevent leakage of the materials being transported. This is particularly the case when handling potentially hazardous (i.e. flammable) or toxic materials.

For reasons of safety, it is often necessary to periodically test the integrity of the welds used in joining the various pieces of equipment (such as pipes, vessels, flanges and the like) together. However, a particular problem is encountered when attempting to test the integrity of welds used in joining a nozzle to a pipe or vessel. Nozzles generally comprise a short conduit with one end inserted into or abutting an opening in a pipe or vessel and an opposite end having a flange. The joints between the conduit portion of the nozzle and the pipe or vessel and the flange, respectively, are sealed with welds. As is known in the art, nozzles can range in size from less than an inch to up to several feet in diameter.

The prior art teaches various tools for conducting weld integrity tests on conduits. For example, U.S. Pat. Nos. 6,131, 441 and 5,844,127 (Berube and Carson) (the entire disclosures of which are incorporated herein by reference) teach weld testing tools which isolate a particular section of a pipe (for example, a section including a weld) and subject the section to a high pressure fluid within a constrained annular space defined by the tool and the inner surface of the pipe. The pressure of the fluid within the annular space is monitored whereby any pressure drop signifies a leak in the weld.

U.S. Pat. No. 5,024,079 (Dufort) teaches a tool for testing welds on flanged pipes. The tool includes a first piece that is inserted into the flange and which extends partially into the length of the pipe. The first piece is sealed against the pipe wall. A second piece of the tool is positioned outside of the pipe and bears against the flange opening. The two pieces are connected together by a shank, which extends axially through pipe and is of a much smaller diameter than the pipe. This arrangement creates an annular space which is filled with a pressurized fluid. This reference does not teach a tool that can be used for a nozzle provided on a vessel. Further, since the tool must be sized with respect to the diameter of the pipe being tested, the resulting weight of a tool for large diameter equipment renders the tool very difficult to install and use.

Figure 1:
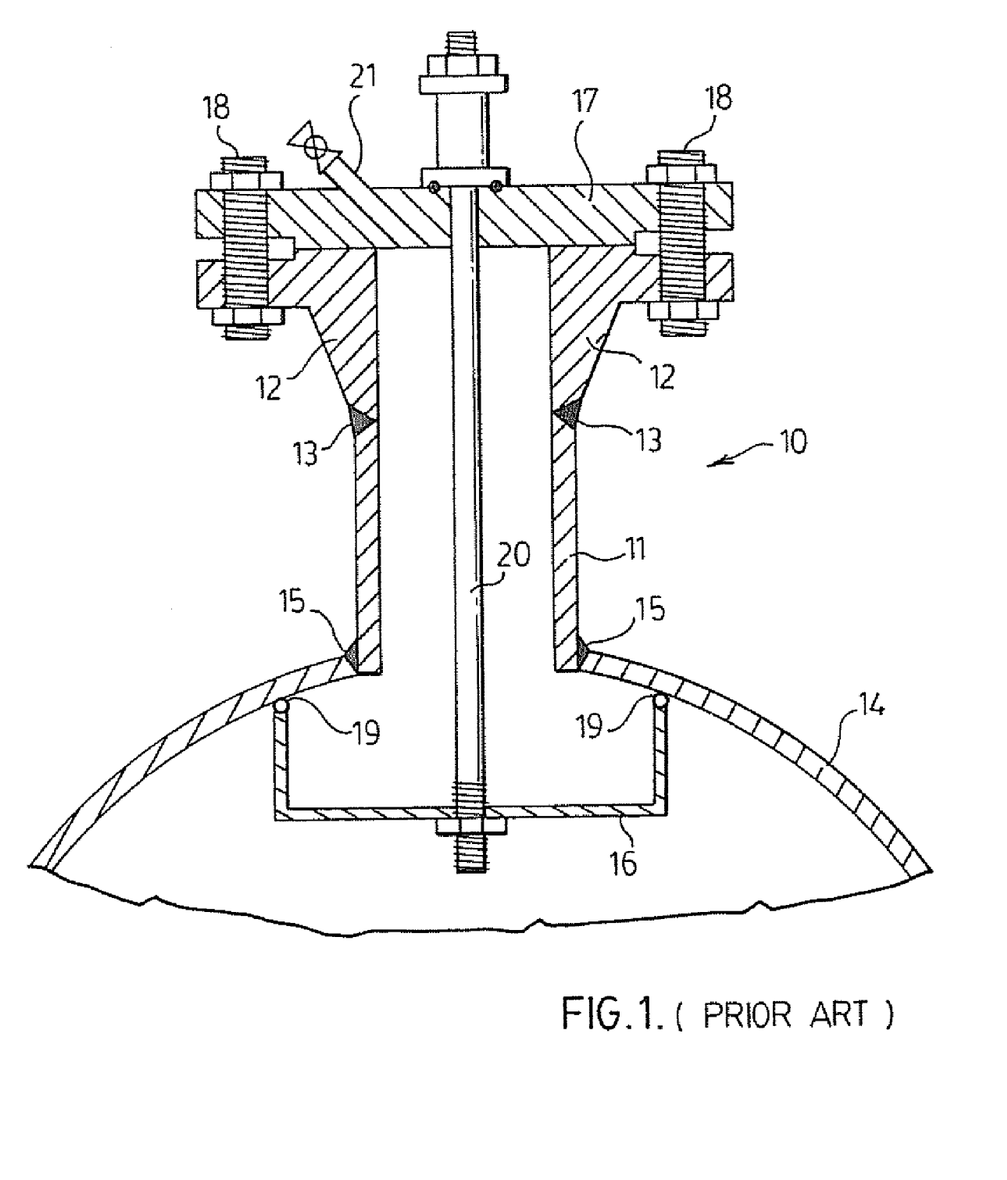
FIG. 1 is a cross sectional view of a weld testing apparatus for nozzles as known in the prior art.

U.S. Pat. No. 6,367,313 (Lubyk) teaches another test tool, or plug, for testing the integrity of welds in a pipe. The tool of this reference is designed to be adjustable to various diameters of pipes but still includes a structure that is similar to that of U.S. Pat. No. 5,024,079 discussed above. This reference also does not teach a tool that can be used on a vessel nozzle and includes the same deficiency of increased weight mentioned above in that a tool for larger diameter pipes U.S. Pat. No. 6,463,791 (Berube and Carson) (the entire disclosure of which is incorporated herein by reference), however, does teach an apparatus for testing welds used to secure nozzles. As shown in FIG. 1 of this reference, the apparatus comprises a first seal plate that is placed on the inner surface of the vessel (for example) and a second seal plate that is secured to the outer, flange portion of the nozzle. In this manner, the nozzle volume is sealed and a pressurizing fluid is introduced therein. Once the volume is filled, the pressure is monitored as above and any leakage detected. Although this apparatus provides an accurate and efficient means of testing welds on nozzles, the size and weight of the apparatus makes it inconvenient for use on large nozzles.

Further, as will be understood, a testing apparatus, particularly those of larger sizes, requires at least two technicians to properly position the apparatus and to conduct the test. In this case, at least one technician will be located within the vessel, on the inside end of a nozzle, and at least one other technician will be located outside of the vessel, at the flange end of the nozzle. Thus, it is often necessary to provide a means of communication between the technicians to properly co-ordinate the test. Although the nozzle opening itself is one means of communication, many of the prior art apparatus, as discussed above, completely seal the nozzle opening thereby preventing communication there-through. It will be understood that electronic communication devices cannot be used in most cases where flammable vapour residues and the like may exist. Further, by sealing off the larger nozzle openings, the prior art devices also block the quickest means of ingress and egress for the technicians, which could pose a safety hazard.

Thus, a testing tool for nozzles is desired that overcomes some of the deficiencies associated with prior art apparatus.

SUMMARY OF THE INVENTION

In one aspect, the present invention provides a weld testing assembly or apparatus for testing the integrity of welds securing a nozzle to a vessel and the like wherein the assembly includes a first member located outside of the nozzle, a second member located inside the nozzle and an annular tube extending into the nozzle whereby a sealed annular space, encompassing the welds, is created within the nozzle. The sealed space can then be filled with a pressurising fluid and the pressure monitored for indication of leaks.

In another aspect, the invention provides a method of testing welds securing a nozzle to a vessel and the like comprising the creation of a sealed annular space within the nozzle stem encompassing one or more welds and filling the sealed space with a pressurising fluid and monitoring the pressure for indication of leaks.

Thus, in one aspect, the invention provides a weld testing assembly for pressure testing welds securing a nozzle to a vessel, the nozzle having a stem portion welded to an opening in the vessel wall and an opposite flange portion extending outward from the opening, the assembly comprising:

a first anchoring member mountable against the flange portion of the nozzle;

a second anchoring member mountable against the inner surface of the vessel wall and overlapping the opening;

an annular body extending between and connected to the first and second anchoring members, the annular body being adapted to extend through the stem portion when in use;

a first sealing member provided between the annular body and the stem portion; and, a second sealing member provided between the second anchoring member and the vessel wall;

whereby, when the assembly is in position, a sealed area is formed between the second anchoring member, the annular body, and the stem portion; and, one or more ports for filling and pressurizing the sealed area.

Thus, in another aspect, the invention provides a method of pressure testing welds securing a nozzle to a vessel the nozzle having a stem portion welded to an opening in the vessel wall and an opposite flange portion extending outward from the opening, the method comprising:

creating a sealed annular space within the stem portion, the space being bounded by the inner surface of the stem wall, the annular space encompassing a region containing one or more of the welds;

filling the annular space with a pressurising fluid;

pressurising the annular space with the fluid and monitoring the pressure.

Thus, in yet another aspect, the invention provides a method of pressure testing welds securing a nozzle to a vessel, the nozzle having a stem portion welded to an opening in the vessel wall and an opposite flange portion extending outward from the opening, the method comprising:

providing a first anchoring member bearing against the flange portion of the nozzle;

providing a second anchoring member bearing against the inner surface of the vessel wall and overlapping the opening;

providing an annular body having an outer diameter less than the inner diameter of the stem portion;

inserting the annular body generally coaxially into the stem portion;

forming a sealed area between the second anchoring member, the annular body, and the stem portion by creating a first seal between the annular body and the stem portion and by creating a second seal between the second anchoring member and the inner surface of the vessel wall; and, filling and pressurising the sealed area.

BRIEF DESCRIPTION OF THE DRAWINGS

These and other features of the invention will become more apparent in the following detailed description in which reference is made to the appended drawings wherein.

DETAILED DESCRIPTION OF THE INVENTION

Throughout the description of the invention the following terms will be assumed to have the following associated meanings:

"Vessel"—will be understood to mean any equipment or apparatus to which a nozzle is attached. As such, the term "vessel" will include vessels per se, pipes, drums, and any other similar equipment. It will be understood that the term "vessel" is used herein simply as a convenient way to encompass all such equipment or apparatus.

"Annular"—this term is used to describe a body having at least one outer diameter and at least one inner diameter. Thus, an "annular tube" will be assumed to be a hollow tube with an inner and outer diameter. An "annular disc" will be assumed to be an object having an outer diameter and a central aperture thereby providing an inner diameter.

"Disc"—this term will be used to denote a generally two dimensional circular object as well as other "discs" including a circumferential flange etc.

FIG. 1 illustrates a nozzle weld testing apparatus as known in the art and as taught in U.S. Pat. No. 6,463,791. As shown, the nozzle 10, includes a stem 11 and a flange 12 joined to one end of the stem by a weld 13. The opposite end of the stem is joined to an opening in the vessel 14 by means of another weld 15. The testing apparatus includes a first, inside seal plate 16 that is placed within the vessel 14 so as to seal the inside end of the nozzle. The apparatus also includes a second, outside seal plate 17 that is positioned against the flange 12 and joined thereto by means of bolts 18. It will be understood that gaskets, O-rings, and other such sealing members will be used as known in the art to achieve the desired sealing. For example, a seal between the inside plate 16 and the wall of the vessel 14 may be achieved using an O-ring 19. The inside and outside seal plates 16 and 17 are joined together by one or more tie rods 20. Tightening of the tie rod 20 causes the inside plate to be sealed against the inner wall of the vessel. This results in the volume of the nozzle 10 being sealed off. A port 21 is used to introduce a pressurizing fluid into the nozzle volume. In order to conduct the test, the pressure within the nozzle is raised to the desired level and monitored. Any pressure drop or leakage is indicative of a weakness or leakage in the welds 13 and 15.

As discussed above, the prior art apparatus, although efficient and accurate, requires complete closure of the nozzle opening and, particularly for larger nozzles, cumbersome equipment that is difficult to manoeuvre and install. A farther problem arises in cases where the pipe portion of the nozzle extends partially into the interior of the vessel. As can be seen, such an arrangement may prevent the apparatus from being used if a proper seal cannot be achieved between the inside plate 16 and the vessel wall.

Figure 2:
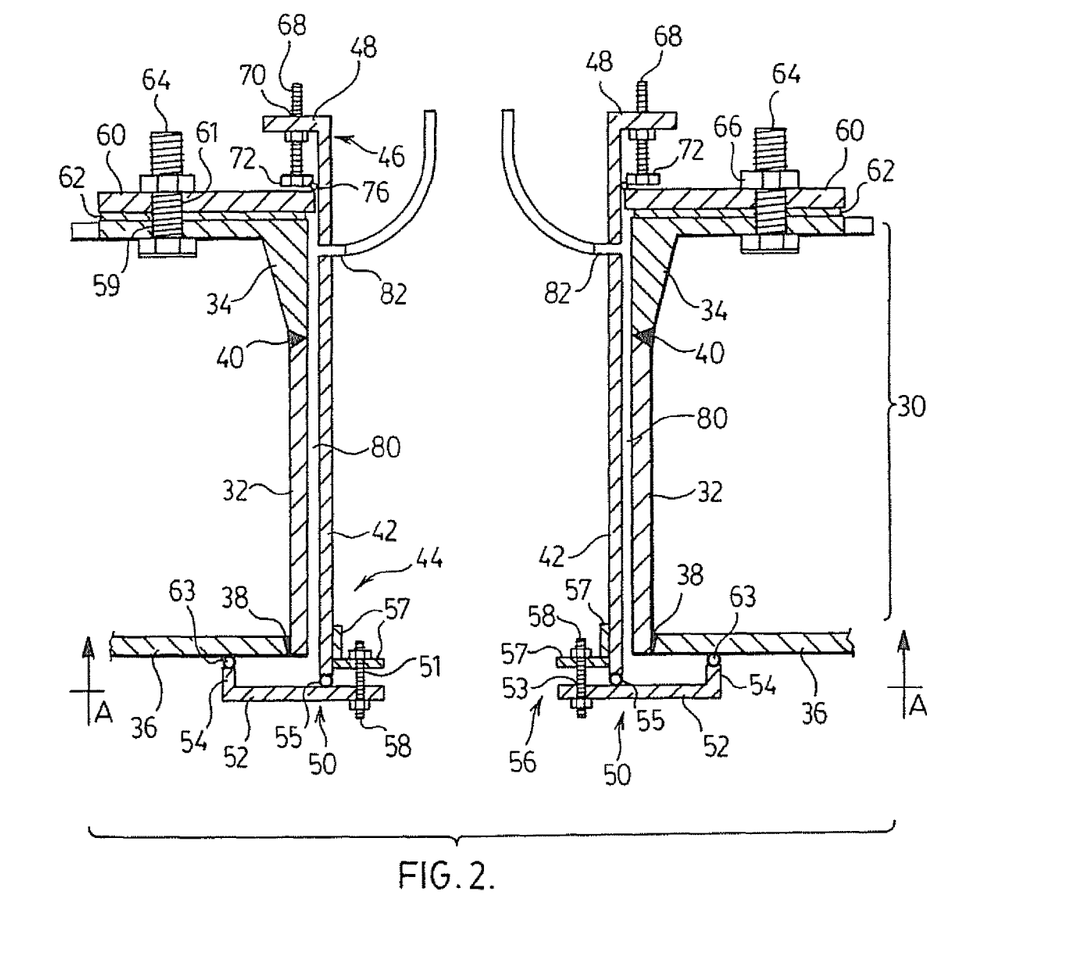
FIG. 2 is a cross sectional view of the apparatus of the invention according to one embodiment.

FIG. 2 illustrates a nozzle testing tool according to one aspect of the present invention. As shown, a nozzle 30 includes a pipe portion, or stem 32 and a flange 34, similar to the nozzle illustrated in FIG. 1. The stem 32 is connected to an opening in a vessel wall 36 by means of welds 38. The flange 34 of the nozzle is connected to the stem 32 by welds 40. For the purposes of this description, the example of a nozzle attached to a vessel will be used herein. However, it will be understood that the nozzles being tested by the apparatus of the present invention can be attached to various other equipment such as another pipe etc.

The apparatus of the invention is shown having a main body comprising longitudinally extending annular body 42 generally having the form of a pipe and being generally coaxial with the stem 32 of the nozzle. The pipe 42 is chosen or sized to have an outer diameter that is less than the inner diameter of the stem 32 of the nozzle. The pipe 42 has a first, inside end 44 that, when in use, opens into the vessel 36 and an opposite second, outside end 46 that, when in use, opens to the atmosphere. The outside end 46 of the pipe 42 includes a flared portion or flange 48 having an outer diameter greater than that of the pipe 42. The pipe flange 48 is preferably formed integral with the pipe 42; however, it will be understood that the pipe flange 48 can be either welded or otherwise connected to the pipe 42 in a sealing arrangement.

The apparatus further includes an inside seal plate, or cap 50 that, when the apparatus is in use, is adapted to be located within the vessel 36. The cap 50 preferably comprises a disc shaped plate section 52 and a ring portion 54 that is adapted to abut the inner surface of the vessel wall 36. The ring 54 extends perpendicular to the plate 52 and may be integral with plate 52 or connected thereto by welds or other connecting means. The plate includes a generally central opening 56 which is preferably of a smaller diameter than the diameter of the pipe 42 described above. The cap 50 can be a single piece or be comprised of two or more sections (as discussed further below) that can be joined together to form a unitary body. Normally, such pieces are inserted into the vessel and joined together there-in. This feature is advantageous in situations where the nozzle opening is fairly large and it is more convenient to handle smaller sections of the cap 50. In other cases, the sections of the cap can be passed through the nozzle itself and joined together from within.

Figure 5:
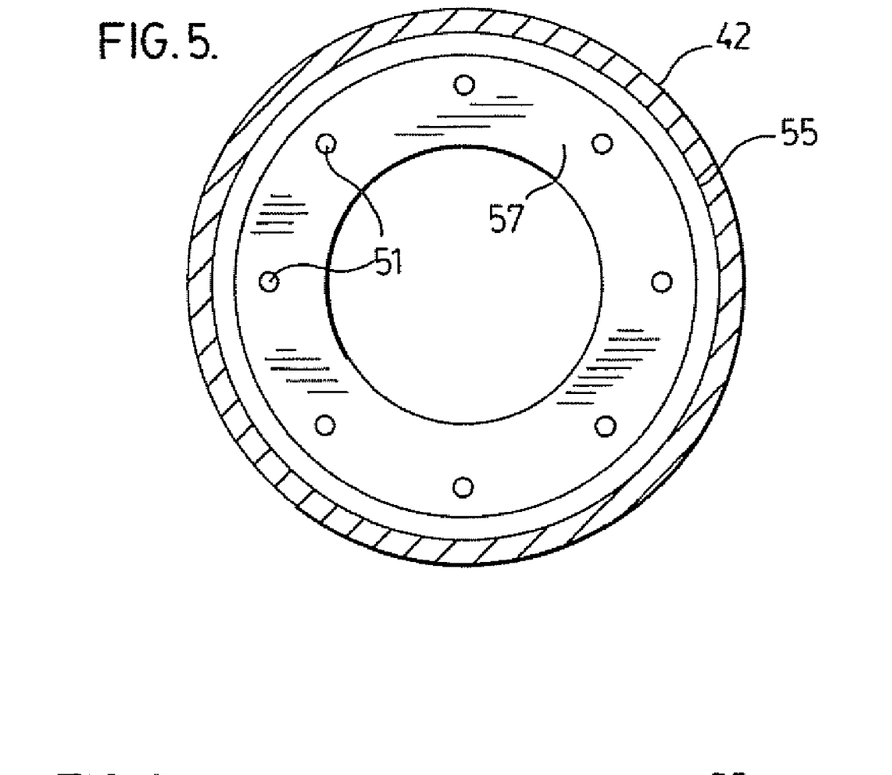
FIG. 5 is an end view of the pipe of the apparatus taken along the line A-A of FIG. 2.

The pipe 42 of the apparatus further includes a flange 57. The flange 57 is provided on the inner surface of the pipe 42, proximal to the first end 44, and extends radially inwardly. The flange 57 may be integrally formed with the pipe 42 or connected thereto by welds or other means. As shown in FIGS. 2 and 5, the flange 57 comprises a ring having a general "L" shape cross section, with one side welded to the inner surface of the pipe 42. It will be understood that the flange 57 can be provided in two or more pieces to facilitate transport and handling. However, when installed, the pieces will combine to form a ring. Further features of the cap 50 are discussed below with reference to FIGS. 6a and 6b.

The flange 57 of the pipe 42 and the plate 52 of the cap 50 are provided with matching holes, 51 and 53, respectively, whereby, when the holes are aligned, bolts 58 can extend there-through so as to secure the pipe 42 to the cap 50. When attached, the cap 50 is oriented so that the ring 54 extends in the same direction as the pipe 42.

The apparatus of the invention also preferably includes a bearing ring 60 located, when the apparatus is in use, proximal to the outer end of the pipe 42. The bearing ring 60 includes an inner diameter that is larger than the outer diameter of the pipe 42 so that the ring can slide over the pipe. The bearing ring 60 includes holes 61 that correspond with holes 59 that are normally provided on the flange 34 of the nozzle.

The apparatus of the invention will now be described further with reference to its use. First, the bearing ring 60 is slid over the pipe 42 and moved toward the flange 48. The pipe is then inserted into the nozzle from the outside whereby, when fully inserted, the bearing ring 60 bears against the outer surface of the flange 34 of the nozzle. From the inside of the vessel, the cap 50 is positioned over the inner end 44 of the pipe 42 such that the holes 51 in the flange 57 of the pipe 41 align with holes 53 in the plate 52. To assist in such positioning and alignment of the holes 51 and 53, both the pipe 42 and cap 50 may be provided with locating pins as known in the art. The cap 50 is positioned so that the ring 54 extends towards the vessel wall 36. Once the holes 51 and 53 are aligned, the bolts 58 are inserted there-through and the cooperating nuts tightened so as to force the end of the pipe 42 against the plate 52. A sealing element such as an O-ring 55 is positioned between the end of the pipe 42 and the plate 52 so that, once the bolt 58 are tightened, a seal is produced between the end of the pipe and the plate 52. The O-ring 55 is preferably located within a recess or race provided at the end of pipe 42 and/or on the plate 52. An O-ring 63 or other such sealing element is also provided at the edge of the ring 54 abutting the inner vessel wall 36. The O-ring 63 is preferably located within a recess or race on the edge of the ring 54 abutting the inner surface of the vessel wall.

At the opposite end 46 of the pipe, another securing activity is required. Firstly, the bearing ring is oriented so as to align the holes 61 provided thereon with holes 59 that are normally found on flange 34. As illustrated in FIG. 2, a gasket 62 is provided between the bearing ring 60 and the flange 34. The gasket can be any type of sealing element as known in the art, such as a washer or an O-ring, and can be provided in the shape of a ring (which would require sliding the gasket over the pipe prior to insertion into the nozzle) or in any other shape known to persons skilled in the art that would lead to the desired seal between the bearing ring 60 and the flange 34. The gasket 62 is shown as substantially covering the face of the flange 34. However, it will be understood that the sizing of the gasket will be apparent to persons skilled in the art.

Once the holes 61 and 59 are aligned, bolts 64 are inserted there-through and secured with cooperating nuts 66. The nuts are tightened to achieve a seal between the bearing ring 60 and the flange 34. It will be understood that the securing of the bearing ring can be done before, after or during the step of securing the cap 50 to the inner end of the pipe 42. In the illustrated embodiments, the nuts and bolts, 66 and 64, respectively, provide a mechanical means of sealing the bearing ring 60 to the flange 34. In other embodiments, the nuts and bolts can be replaced with hydraulic clamps and the like. Other clamping mechanisms will be apparent to persons skilled in the art that will also serve to seal the bearing ring 60 to the flange 34.

Figure 3:
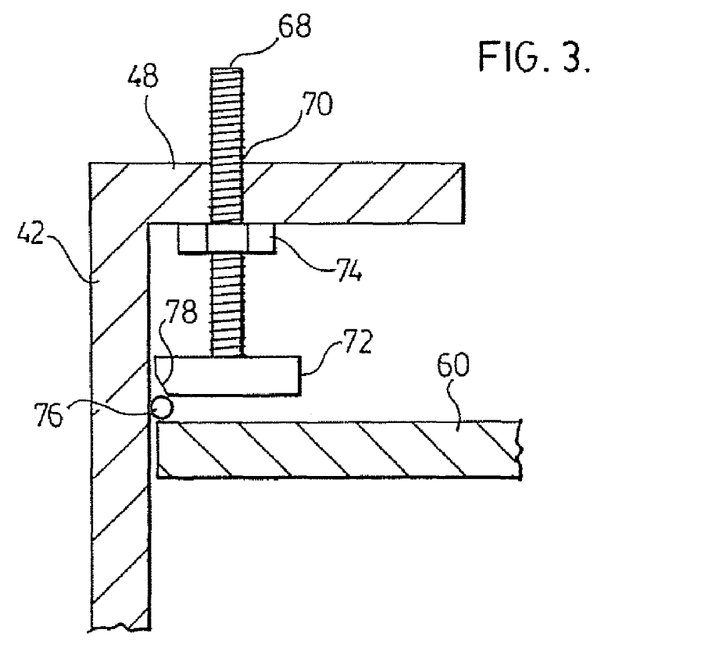
FIG. 3 is a cross sectional view of the jack bolts of the apparatus.

Once the cap is secured to the inner end 44 of the pipe 42 and the bearing ring is secured to the flange 34 of the nozzle, the apparatus can then be secured in position. To achieve this, a number of jacking bolts 68 are provided between the pipe flange 48 and the bearing ring 60. The jacking bolts 68 extend through holes 70 provided in the pipe flange 48 and are provided with shoes 72 abutting the bearing ring 60. The jack bolts 68 and shoes 72 are more clearly illustrated in FIG. 3. As shown in FIG. 3, each jack bolt includes a cooperating nut 74, which, when tightened, forces the shoe 72 against the bearing ring 60. A sealing element such as an O-ring 76 is provided between the shoe 72 and the surface of the bearing ring 60 so as to form a seal there-between. As shown in FIG. 3, the shoe 72 preferably includes a wedge or bevel 78 on its surface abutting the bearing ring 60 and adjacent the pipe 42. In this arrangement, as the shoe is driven towards the bearing ring 60, the wedge 78 serves to deform the O-ring 76 and force it to form a seal between the bearing ring 60 and the outer wall of pipe 42. In other embodiments, the bolts 68 can be replaced with other mechanical or hydraulic devices that achieve the same purpose.

As will be understood by persons skilled in the art, due to the fact that the bearing ring 60 bears against the nozzle flange 34, the tightening of the nuts 74 causes the pipe 42 to move outwardly away from the nozzle 30. As such, the cap, being secured to the pipe 42, is thereby forced against vessel wall 36 and, with the O-rings 63, causes a seal to form there-between.

The shoe 72 can be provided in a variety of structures. For example, the shoe may comprise a single piece with a plurality of shoes being provided alone the circumference of the pipe 42. In the preferred embodiment, the shoe comprises a single ring that is tightened by a plurality of bolts 68. A ring structure for the shoe 72 serves to apply an even pressure on the O-ring 76 and to establish a uniform seal around the pipe 42.

As indicated above, the pipe 42 of the invention is sized to be smaller in outside diameter as compare to the inside diameter of the nozzle stem 32. As such, and as illustrated in FIG. 2, a generally annular space 80 is created between the pipe 42 and the nozzle 30. The sealing of the space 80 is achieved by the O-rings (or other such sealing elements) 55, 63, and 76 and the gasket 62. The pipe is provided with one or more openings or ports 82 that open into the annular space 80. Preferably, two ports 82 are provided, one being connected to a pressurized fluid source (not shown) and the other serving as a vent for the space 80. It will be apparent to persons skilled in the art that the actual number of ports 82 can be varied. Further, although the ports 82 are illustrated as being provided on the pipe 42, it will be understood that one or more ports can also be provided at various other locations such as on the cap 50 or the pipe flange 48. It will further be understood that one or more ports can be provided with pressure release valves.

In operation, once the apparatus is secured to the nozzle and the annular space 80 is formed and sealed off from the environment, a pressurized fluid is introduced into the space 80. If one or more vent ports exist, any air in the space can be easily evacuated. If only one port is used, such evacuation can be accomplished in a step wise manner of filling and evacuating. Once the space 80 is filled and pressurized, the pressure is monitored by means of one or more gauges (not shown). Any drop in pressure signifies a potential leak in one or both of welds 38 and 40.

As will be understood by persons skilled in the art, the apparatus of the present invention provides a number of advantages over the prior art devices. For example, by maintaining the lumen of pipe 42 open, a clear means of communication is provided between technicians on the inside of the vessel and those outside conducting the tests. Further, for nozzles having a large enough opening, the present invention provides a means for personnel to enter and exit the vessel through the lumen of the apparatus without having to create other openings. In cases where small nozzles are being tested, the opening may not be large enough for a person to pass but will be sufficient to provide a simple means of communication for personnel on both sides of the nozzle. In addition, with the present invention, since the testing fluid occupies only an annular space adjacent the pipe wall instead of the entire volume of the nozzle being tested, the volume of pressurizing fluid required is considerably reduced as compared to prior art devices. Further, by avoiding the need for sealing the entire opening of the nozzle (by using the solid plates of the prior art), the weight of the apparatus is also considerably reduced.

In the above description and the accompanying figures, the vessel is shown as being flat in the region of the nozzle. However, as will be understood, and as shown in FIG. 1, any vessel geometry can be accommodated. It will also be understood that the shape of the inside seal plate or cap 50 will be chosen to suit the particular vessel geometry in question.

Figure 4:
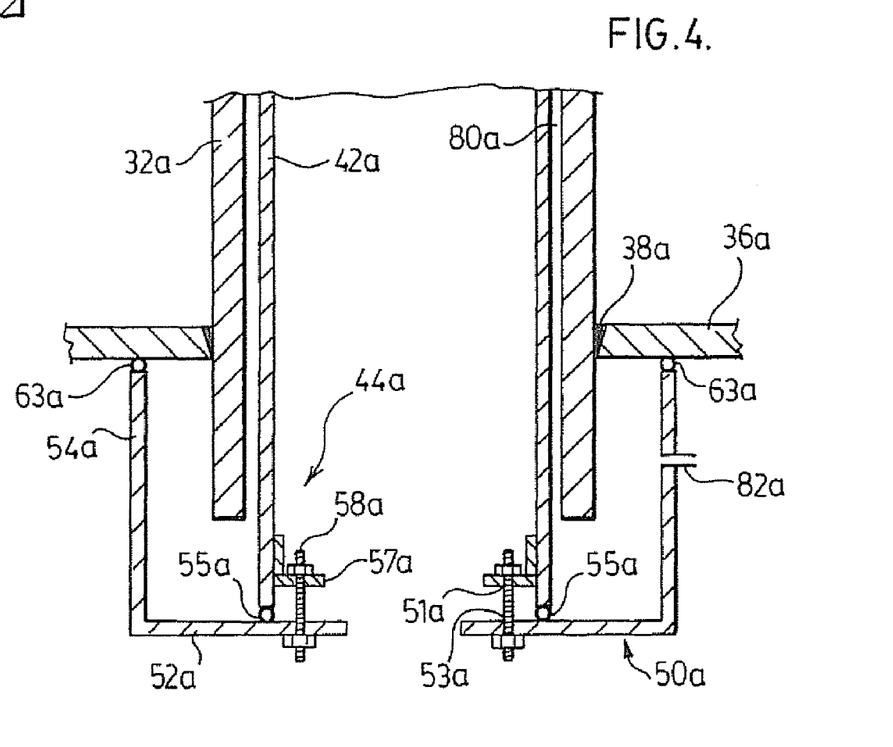
FIG. 4 is a partial cross sectional view of another embodiment of the invention.

FIG. 4 illustrates another embodiment of the invention for accommodating nozzles wherein the stem projects into the vessel wherein like elements are referred to using like reference numerals but with the letter "a" added for clarity. In this embodiment, the stem 32a of the nozzle extends partially into the vessel beyond the vessel wall 36a. Thus, the cap 50a is provided with an elongated ring 54a (i.e. of a greater width than with the previously described ring 54) so that it can envelope the extension of the stem 32a and still form a seal with the vessel wall 36a.

FIG. 4 also illustrates an embodiment wherein a port 82a is provided on the cap 50a as described above. For example, the apparatus (either that of FIG. 2, FIG. 4 or any other embodiment described herein) can include a filling port on the tube 42, 42a and a vent port on the cap 50, 50a. The opposite arrangement is also possible.

FIG. 5 illustrates an end view of the pipe 42 of the invention as seen from the inside end 44, as seen from the view A-A of FIG. 2. FIG. 5 shows the flange 57 and holes 51. Also shown is the O-ring 55, which can be provided on the end of the pipe 42. It will be appreciated throughout this discussion that the relative dimensions and number of bolts etc. will vary depending on the specific application of the apparatus of the invention. For example, FIG. 5 depicts eight holes (51) being used. However, the number of holes will vary depending on the overall diameter of the apparatus.

Figure 6:
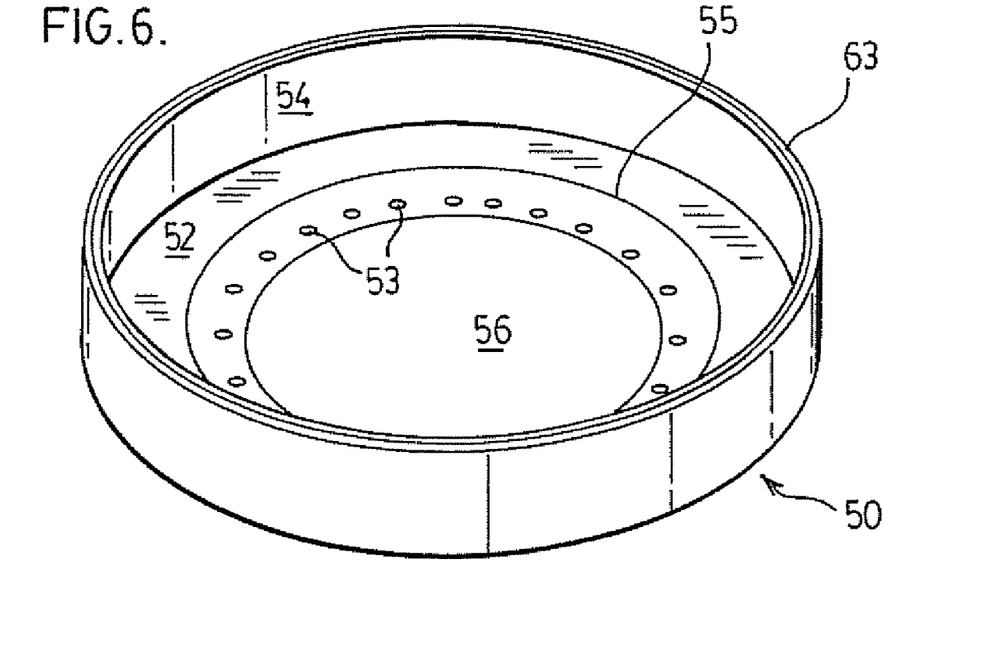
FIG. 6 is an inside perspective view of the cap of the apparatus according to one embodiment.

FIG. 6 illustrates a cap 50 of the invention when provided as a single piece. As shown, the cap includes the seals 55 and 63 as described above.

Figure 7:
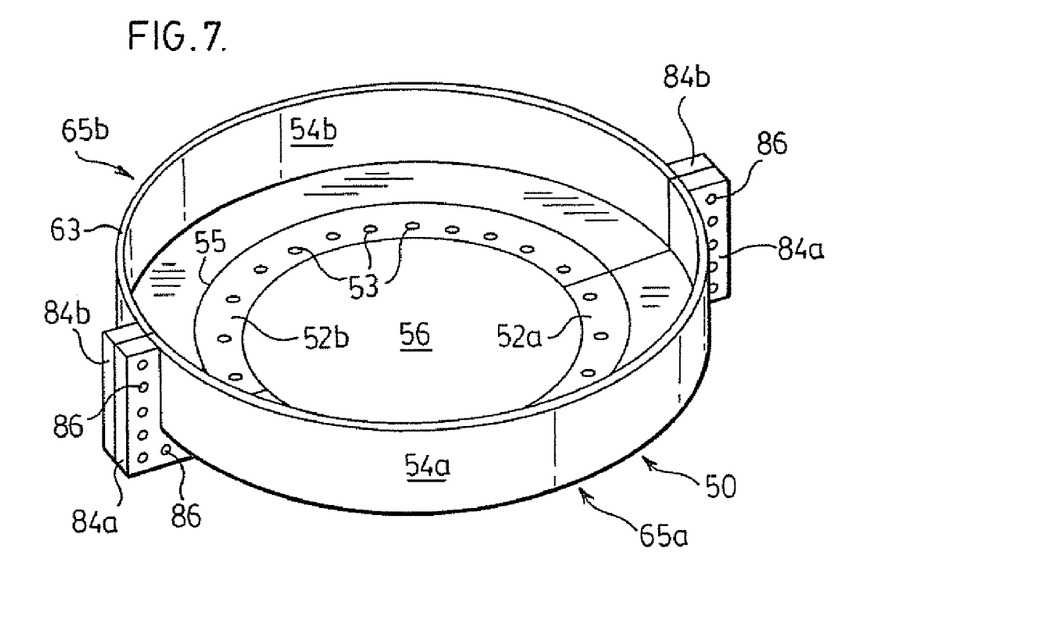
FIG. 7 is an inside perspective view of the cap of the apparatus according one embodiment.
Figure 8:
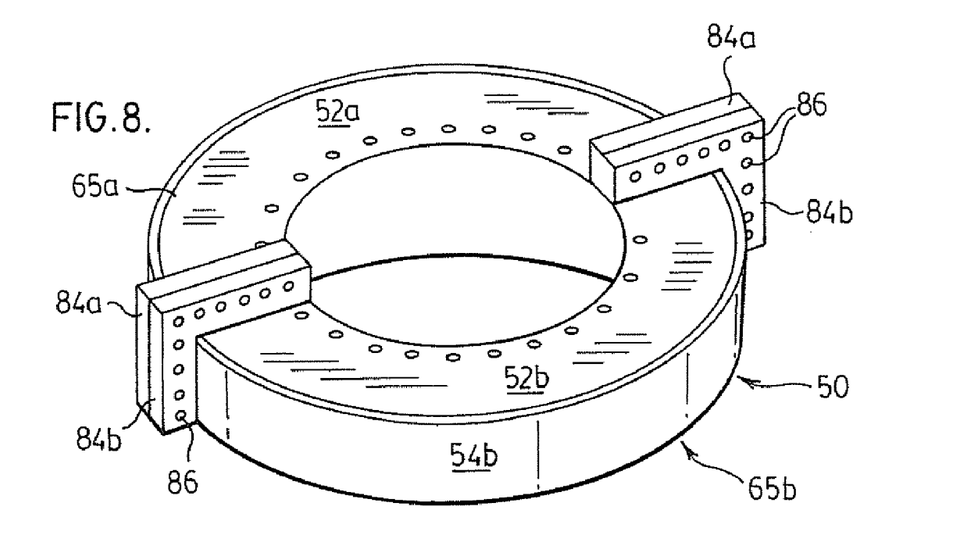
FIG. 8 is an outside perspective view of the cap of FIG. 7.
Figure 9:
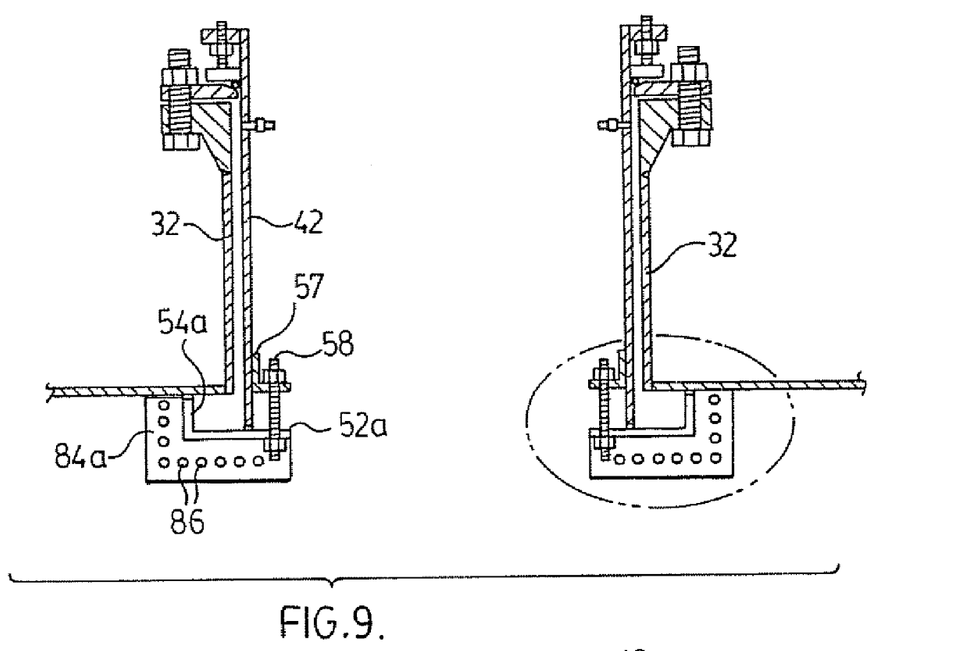
FIG. 9 is a cross sectional view of the cap of FIG. 7 when in use.
Figure 10:
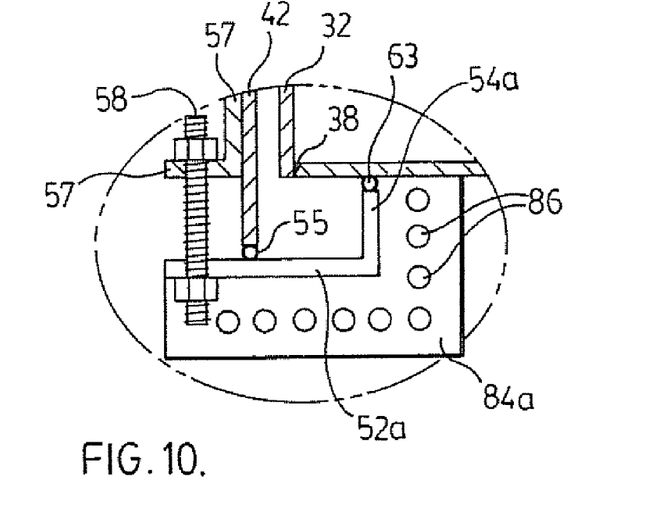
FIG. 10 is a partial cross sectional view of a detail from FIG. 9.

FIGS. 7 to 10 illustrate an embodiment of the cap, designated as 50 of the invention wherein the cap is provided in two sections. As shown in FIGS. 7 and 8, the two halves, 65a and 65b, of the cap 50 are each provided with flange-like extensions 84a and 84b, respectively, each with one or more holes 86 through which are passed connecting bolts (not shown). The bolts are used to assemble the pieces 65a and 65b together to form the cap 50. By providing a cap 50 in two (or more) pieces as shown in FIGS. 7 and 8, the cap can be more easily handled as discussed above. Further, if the nozzle opening is to be used for entrance into the vessel, then the pieces of the cap 50 can be transported into the vessel through the nozzle opening and assembled within the vessel. FIG. 7 illustrates the seats 55 and 63 used with the cap 50c, as described above. As mentioned previously, the seals 55 and 63, typically comprising O-rings, are provided in recesses FIG. 9 illustrates the two piece cap 50c in use. As can be seen, the split embodiment of the cap is used in the same manner as that described above such as in FIG. 2. FIG. 10 illustrates an enlarged view of a section from FIG. 9 showing the seals 55 and 63. As mentioned above, seal 55 is preferably located within a recess or race provided on the inner end 44 of the pipe 42 (that is the end positioned within the vessel) and/or on the plate 52 (formed by combining the plate portions 52a and 52b of cap sections 65a and 65b). Further, the seal 63 is preferably located within a recess or race provided on the edge of ring 54 (formed by combining ring portions 54a and 54b of cap sections 65a and 65b).

Figure 11:
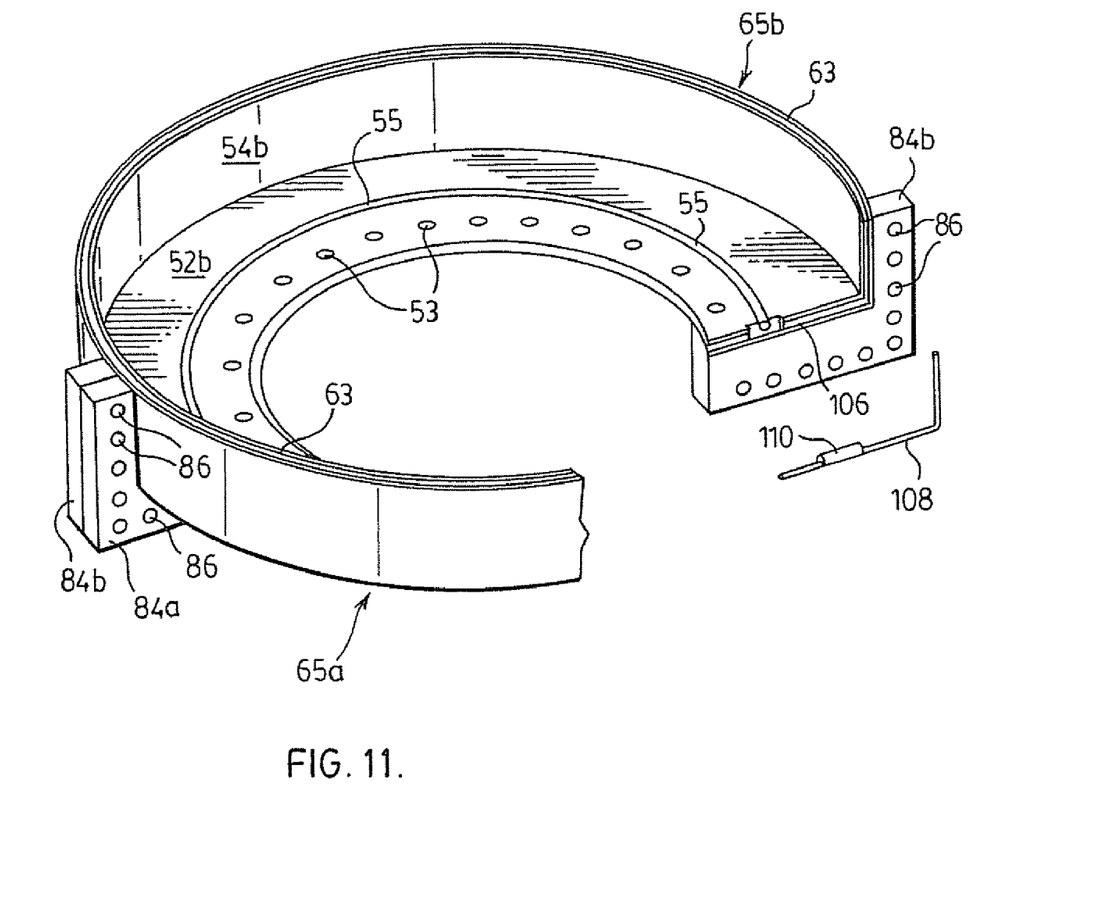
FIG. 11 is a cut away perspective view of the cap of FIG. 7.

In the split cap illustrated in FIGS. 7 to 10, seal would preferably be used at the seam formed from the two (or more) sections. This seal is illustrated in FIG. 11. As shown in FIG. 11, a recess or race 106 is provided on the abutting ends of each section 65a and 65b. A resilient sealing member 108 is located within the race 106. The sealing member, as shown, would generally be "L" shaped so as to match the shape of the ring 54 and plate 52 sections. The sealing member 108 would preferably comprise a section of an O-ring seal. As shown, the sealing member 108 also includes an enlarged section 110 to accommodate the "crossover" point between the sealing member 108 and the sealing member 55 provided on the plate 52.

Figure 12:
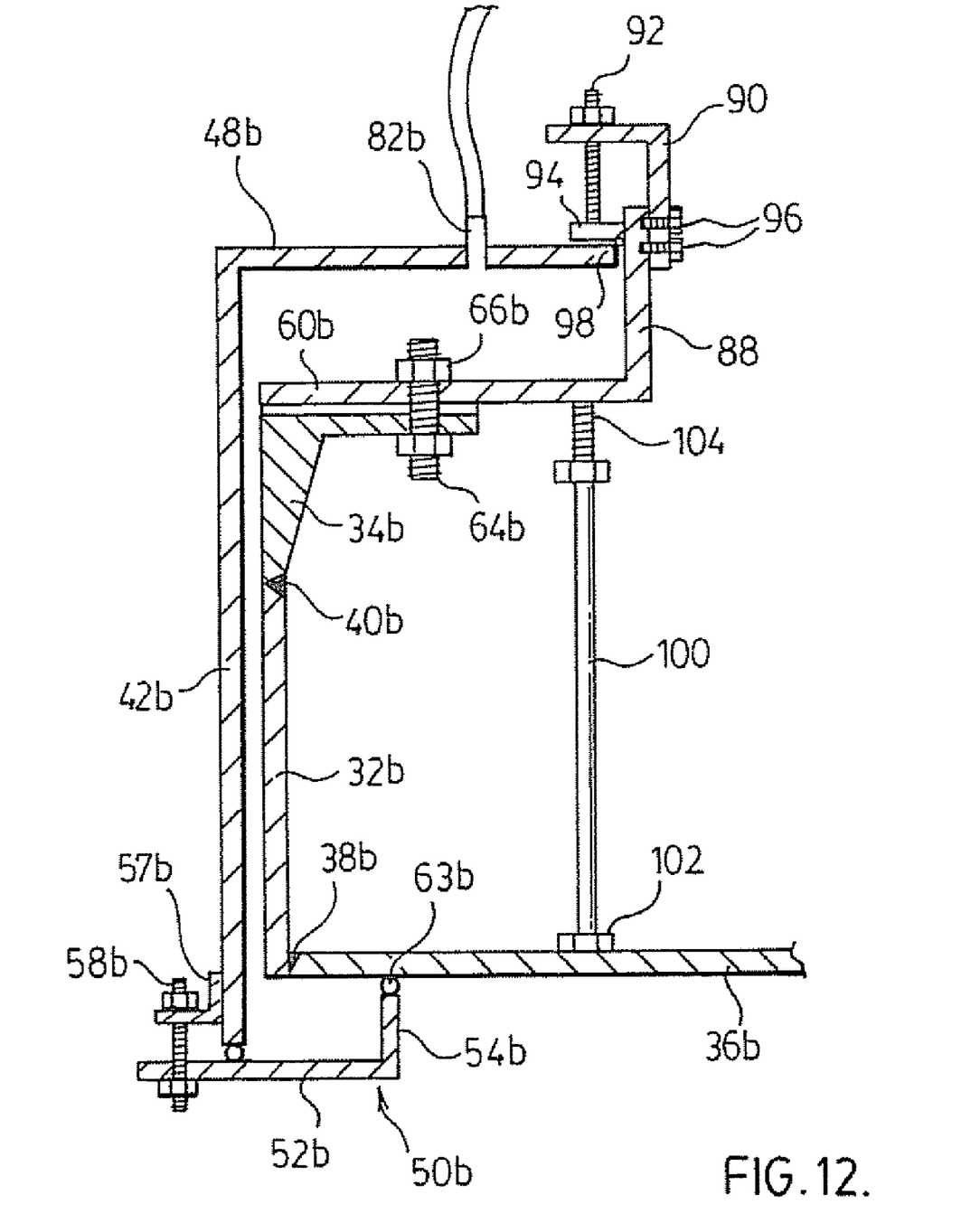
FIG. 12 is a partial cross sectional view of another embodiment of the invention.

A further embodiment of the invention is illustrated in FIG. 12 wherein elements equivalent to those described earlier are identified with like reference numerals but with the letter "b" added for clarity. For ease of viewing, FIG. 12 illustrates one half of the nozzle and apparatus combination. In this embodiment, the pipe 42b of the apparatus is provided with a larger flange 48b as illustrated in FIG. 12. Further the bearing ring 60b of this embodiment includes a perpendicularly extending flange 88, which extends away from the nozzle. A retaining ring 90 is attached to the flange 88 and includes a bolt 92 having an associated shoe 94. Retaining ring 90 can be secured to the flange 88 by means of bolts 96 as shown in FIG. 12 or by any other means as will be apparent to persons skilled in the art. As in the previously described embodiments, the shoe 90 is preferably a flat ring.

In using the apparatus of FIG. 12, the bearing ring 60b, with the associated flange 88, is first secured to the flange 34b outer surface. The pipe 42b is then inserted into the nozzle opening and the cap 50b secured thereto as described above. The retaining ring 90 is then attached to the flange 88 of bearing ring 60b. Preferably, the bolt 92 with associated shoe 94 is connected to the retaining ring 90 prior to attachment to flange 88. The bolts 92 are tightened using nuts until a seal is established. The seal is achieved by means of deforming a sealing element such as an O-ring 98 as shown in FIG. 12. Subsequently, a pressurizing fluid is introduced through port 82b to fill the space created between the apparatus and the nozzle. As will be understood, one or more other ports may be provided at different locations of the apparatus. The increase in pressure causes the pipe flange 48b to bear against the shoe 94 thereby further increasing the sealing force resulting from the O-ring 98. In the embodiment shown in FIG. 12, the apparatus is further provided with a number of support rods 100 having a first end 102 bearing against the vessel wall 36b and an opposing end 104 bearing against the bearing ring 60b. Preferably, six or more support rods 100 are provided in a spaced apart manner around the circumference of the bearing ring 60b. The support rods 100 serve to brace the bearing ring 60b against the vessel wall 36b in the event the testing pressure causes undue lateral stresses on the apparatus. For example, as will be understood, if very high pressures are used, the bearing ring 60b may be subjected to a turning moment about the flange 34b. The support rods 100 serve to prevent such movement. In another embodiment, the support rods 100 may be loaded so as to provide an axial pressure between the bearing ring 60b and the vessel wall 36b. Such a loading (which can be applied by means of springs, jacks, screws and other means as will be apparent to persons skilled in the art) serves to apply a separating force between the bearing ring 60b and the vessel wall 36b, thereby applying a further stress on the welds 38b and 40b. In other words, apart from the radial stresses applied in the course of testing process as described above, the rods 100 can apply axial, or longitudinal stresses on the welds as well. It will be understood that the term "axial" or "longitudinal" is used in reference to the longitudinal axis of the nozzle. As will be understood by persons skilled in the art, this extra stress simulates extreme conditions under which the welds can be tested. In the above description, axial stresses are applied by the support rods 100. However, other means of applying axial stresses will be apparent to persons skilled in the art. For example, any form of external apparatus can be used to "pull" the nozzle away from the pipe. Such apparatus will result in axial stresses similar to those provided by the rods 100. In an alternate embodiment, the rods 100 can be replaced with hydraulic jack mechanisms.

Figure 13:
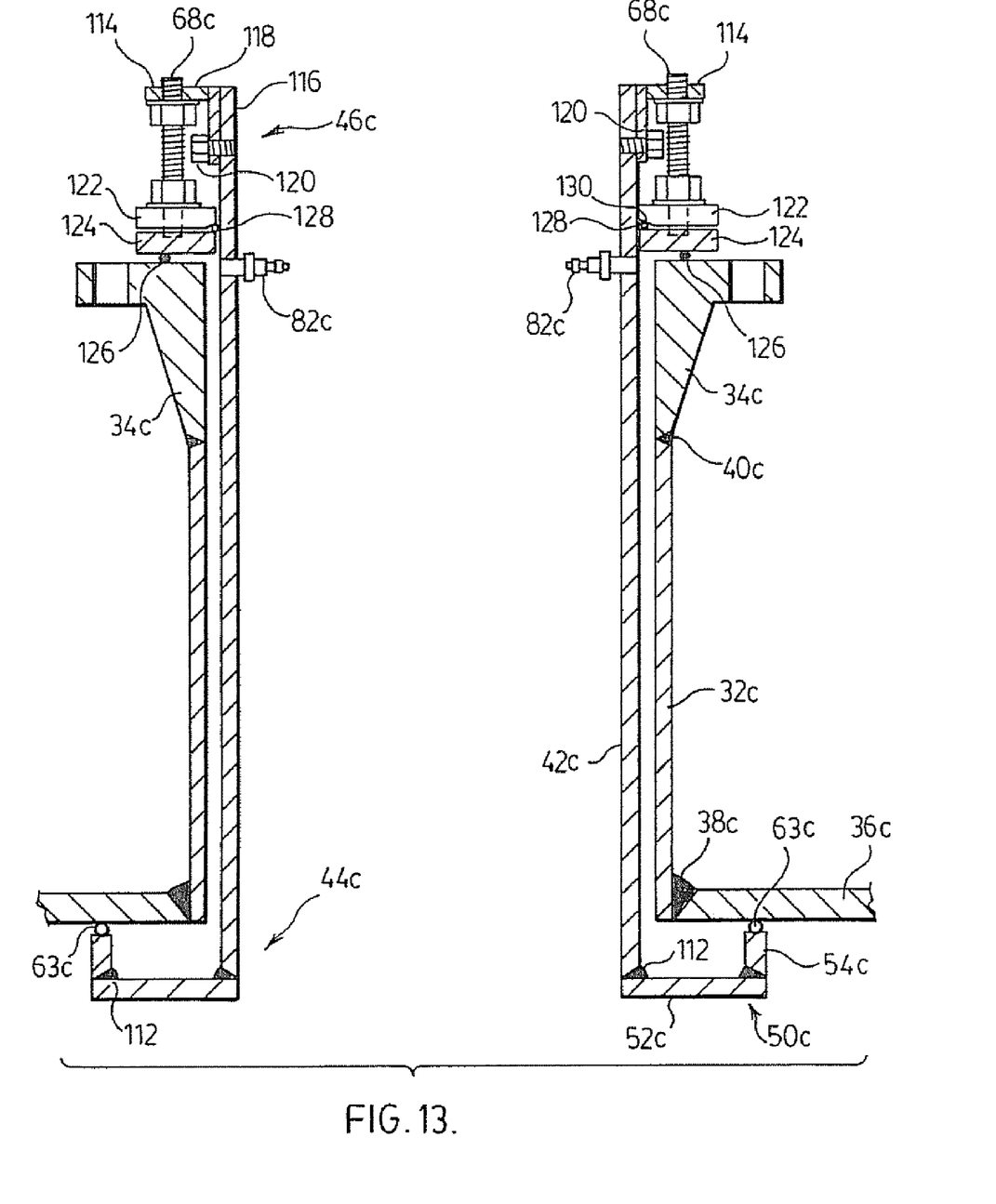
FIG. 13 is a cross sectional view of the apparatus of the invention according to another embodiment.

FIG. 13 illustrates another embodiment of the invention wherein elements equivalent to those described earlier are identified with like reference numerals but with the letter "c" added for clarity. In the embodiment of FIG. 13, the cap 50c and pipe 42c of the apparatus are connected to form a unitary structure. As shown, the cap 50c is welded to the inner end 44c of the pipe 42c by means of a weld 112. This, therefore, avoids the need for a sealing member between the end of the pipe 42c and the plate portion 52c of the cap 50c. As will be understood, the outside end 46c of the pipe 42c will need to be reconfigured from that shown in FIG. 2. Specifically, since, in this embodiment, the cap 50c is permanently attached to the pipe 42c, the apparatus would need to be inserted through the flange opening from within the vessel 36 (or other pipe or equipment to which the flange is attached). As such, the outside end 46c of the pipe 42c would need to be of a diameter that would permit it to be passed through the opening of the flange 34c. For this reason, the pipe 42c of the embodiment of FIG. 13 includes an outside end 46c that does not have an attached pipe flange (shown as 48 in FIG. 2). Instead, a separate collar 114 is provided for attaching the pipe 42c to the flange 34c.

As shown in FIG. 13, the collar 114 has a generally "L" shaped cross section including a first section 116 adapted to be secured to the pipe 42c and a second section 118, generally perpendicular to the first section, adapted to receive jacking bolts 68c, or other similarly functioning mechanical or hydraulic devices. The first section 116 of the collar 114 can be secured to the pipe 42c by means of bolts 120. It will be understood that any other releasable attachment means can also be provided. As with the embodiment described above in reference to FIG. 2, the jacking bolts 68c serve to position and seal the apparatus against the flange 34c. As with the previous description, the sealing member 76c is pressed against the outside surface of the pipe 42c thereby sealing off a generally annular space between the pipe 42c and the inner surface of the flange.

FIG. 13 also illustrates an alternative to the shoes 72 of FIG. 2. Specifically, the apparatus includes two concentric sealing rings 122 and 124. The first ring 122 is provided adjacent the jacking bolts 68c and serve to force the second ring 124 against the outside face of the flange 34c. A resilient sealing member 126 is provided on the second ring 124 so as to form a seal between the second ring 124 and the flange 34c. In the preferred embodiment, a recess or race is provided on the surface of the second ring 124 in order to locate and accommodate the sealing member 126. A further sealing member 128 is associated with the first sealing ring 122 and serves to form a seal between the first ring 122 and the pipe 42c. To assist in this, the first ring 122 is provided with a wedge or bevelled portion 130 adjacent the pipe 42c so as to force the sealing member 128 against the wall of the pipe 42c. As can be seen in FIG. 13, as the jacking bolts 68c are tightened, the second ring 124 and the sealing means 126 are forced against the flange face and a first seal is formed therebetween. The first ring 122 is similarly forced against the second ring 124 thereby "pinching " the sealing member 128 against the pipe 42c wall thereby creating a second seal. The ports 82c provided on the pipe 42c (or, in other embodiments, on the cap 50c), are then used to fill and pressurize the sealed space between the pipe 42c and the inner flange surface to conduct the integrity tests.

Figures 14, 15, 16:
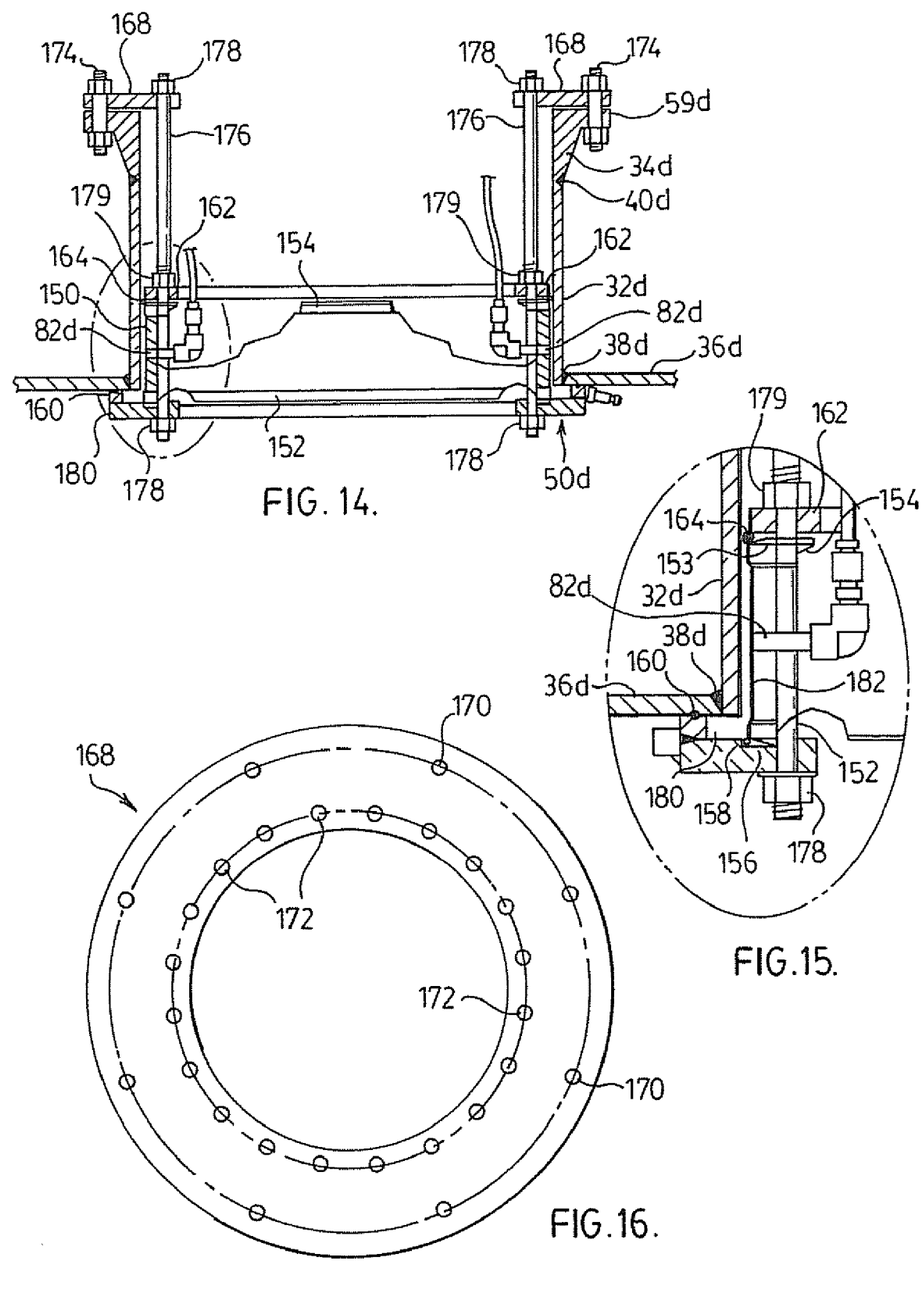
FIG. 14 is a cross sectional view of the apparatus of the invention according to another embodiment.
FIG. 15 is a partial cross sectional view of a detail from FIG. 14.
FIG. 16 is a plan view of the outer plate of FIG. 14.

FIGS. 14 and 15 illustrate a further embodiment of the invention wherein only the weld between the nozzle stem and the vessel is to be tested. In FIGS. 14 and 15, elements equivalent to those described earlier are identified with like reference numerals but with the letter "d" added for clarity. As illustrated, the apparatus of this embodiment includes an annular body 150 that is adapted for insertion within the nozzle stem 32d. The ring 150 includes a first end 152 that extends partially into the vessel 36d to which the nozzle is attached and an opposite second end 154 that is positioned within the nozzle stem 32d. As shown, the annular body 150 is dimensioned to be smaller in diameter than the nozzle stem 32d, thereby leaving a clearance there-between. A sealing plate or cap 50d is provided within the vessel. The cap 50d is comprised of a plate portion 52d and a generally perpendicular ring portion 54d. The plate portion 52d of the cap 50d includes a race 156 adapted to receive the first end 152 of the annular body 150. The race 156 also includes a resilient sealing member 158, such as an O-ring, so as to seal the joint between the cap 50d and the annular body 150. The ring portion 54d of the cap 50d includes a recess or race at the end abutting the vessel wall wherein a resilient sealing member such as an O-ring 160 is provided, thereby enabling a seal to be formed between the cap 50d and the vessel 36d.

A front plate 162 is provided against the second end 154 of the annular body 150. The front plate 162 comprises an annularly shaped disc having an outer diameter that generally corresponds to the diameter of the annular body 150. Preferably, the second end 154 of the annular body includes a bevelled or wedge shaped section 153 that tapers towards the nozzle stem 32d. A resilient sealing member, such as an O-ring 164, is provided in the wedge 153 and is maintained in position by the front plate 162. It will be understood that the wedge 153 directs the deformation of the O-ring 164 against the inner surface of the nozzle stem 32d as the front plate is urged against the second end 154 of the annular body 150. The race 156 on the cap 50d is provided with a similar resilient sealing member, such as an O-ring 166, to enable a seal to be formed between the cap 50d and the first end 152 of the annular body 150. As with the second end, the first end 152 of the annular body may preferably also include a bevelled or wedge portion to direct the deformation of the sealing member 166 as the cap 50d is urged against the first end 152 of the annular body 150.

The apparatus further includes an outer plate 168, comprising an annular disc. The outer plate 168 is located outside of the nozzle and is secured to the flange portion 34d of the nozzle. As shown in FIG. 16, the outer plate 168 includes two series of openings, an outer series 170 and an inner series 172. The outer series of openings 170 is provided closer to the outer diameter of the plate 168 and are aligned with bolt holes 59d provided on the flange portion 34d of the nozzle. In the result, bolts 174 secure the outer plate 168 to the outer surface of the flange 34d. The inner series of openings 172 are generally equally distributed circumferentially. A plurality of tightening bolts 176 extend through the inner series of openings 172. The tightening bolts also extend through openings provided on the annular body 150 and the sealing plate or cap 50d. Either one or both ends of the tightening bolts are threaded and are provided with cooperating nuts 178. It will be appreciated that only one end of the bolts require such threaded ends and nuts although FIGS. 14 and 15 show both ends as being so. The tightening bolts 176 are either completely threaded or include a threaded portion proximal to at least the second end 154 of the annular body 150. Sealing nuts 179 are provided on each tightening bolt 176 as will be described further below.

In the arrangement shown in FIGS. 14 and 15, and as described above, it can be seen that as the nuts on the tightening bolts are tightened, the outer plate 168 and sealing plate 50d are forced together. In so doing and since the movement of the outer plate 168 is hindered by its bearing against the flange portion 34d, the sealing member 160 is forced against the inside surface of the vessel wall 36d thereby forming a seal between the vessel wall 36d and the cap 50d. Once this step is completed, the sealing nuts 179 are tightened thereby urging the annular body 150 towards the cap 50d. In this process, the seals 158 and 164 are each deformed. In the result, a first seal is established between the cap 50d and the first end 152 of the annular body (by means of seal 158) and a second seal is established between the front plate 162, the second end 154 of the annular body 150, and the inner surface of the nozzle stem 32d (by means of seal 164). As can be seen, once the apparatus has been thus positioned, an annular sealed area 180 is formed bounded between the cap 50d, the annular body 150, the front plate 162, and the nozzle stem 32d.

The annular body 150 includes one or more, and, preferably, at least two, ports 82d through which the sealed area 180 can be filled with a testing s fluid and pressurized as described above. In one embodiment, the outer diameter of the annular body may optionally include a recess 182 whereby the separation between the annular body 150 and the nozzle stem 32d is larger to accommodate a larger volume of testing fluid.

It will be appreciated that the embodiment of the apparatus illustrated in FIGS. 14 and 15 is focussed primarily on the testing of the weld 38d joining the base of the nozzle stem 32d to the vessel wall 36d. In the case where the apparatus does not extend up to the upstream welds such as shown at 40d, it will be understood that any other known apparatus may be used for such test. Examples of apparatus that can be used for testing welds 40d are provided in U.S. Pat. Nos. 6,131,441; and 5,844,127.

In a preferred embodiment, the cap 50d is provided with locating blocks 184 so as to facilitate positioning of the apparatus within the vessel.

Although the above description with respect to FIGS. 14 and 15 indicated that the cap comprises a single entity, it will be appreciated that, as discussed above, the cap 50d can be provided in one or more sections can be assembled to ether at the job site (or within the vessel itself). Further, the cap 50d can be comprise separate plate (52d) and ring (54d) section that can be connected together in known ways and with the appropriate seals. Further, the cap 50d can be provided with one or more ports 82d either instead or in addition to those provided on the annular body 150.

It will be understood that the above discussion has used geometric terms such as annular, disc, circumference, etc., for ease of reference. However, these terms should not be construed as limiting the invention to any specific shape of nozzle and various modifications of the apparatus will be apparent to persons skilled in the art to adapt same to any shape or design of nozzles.

Although the invention has been described with reference to certain specific embodiments, various modifications thereof will be apparent to those skilled in the art without departing from the spirit and scope of the invention as outlined in the claims appended hereto. The disclosures of all prior art recited above are incorporated herein by reference in their entirety.

We claim:

1. A weld testing assembly for testing one or more welds securing a nozzle to a vessel, said nozzle having a stem portion welded to an opening in the vessel wall and an opposite flange portion extending outward from said opening, the assembly, when in an installed condition, comprising:
    a generally annular first anchoring member adapted to be sealingly mountable against said flange portion of the nozzle, the first anchoring member including a generally central opening;
    a generally annular second anchoring member adapted to be sealingly mountable against the inner surface of said vessel wall and overlapping the opening in the vessel wall, the second anchoring member including a generally central opening;
    an annular body extending between said first and second anchoring members, said annular body being adapted to extend into the stem portion when in the installed condition, and wherein said annular body includes a lumen extending there-through;
    a first sealing means for forming a seal between said annular body and said first anchoring member or said stem portion; and,
    a second sealing means for forming a seal between said annular body and said second anchoring member;
    whereby, when said assembly is in the installed condition, a sealed annular space is formed between the first and second sealing means, the annular body, and the stem portion, said space being capable of being pressurized for conducting a weld test;
    and wherein, in the installed condition, the generally central openings of the first and second anchoring members and the lumen of the annular body align to form an open channel through the nozzle for allowing communication between the interior and exterior of the vessel during the test.

2. The assembly of claim 1 further comprising one or more ports for filling and pressurizing said sealed space.

3. The assembly of claim 2 wherein said one or more ports are provided on the annular body.

4. The assembly of claim 1 wherein said annular body comprises a pipe extending at least between said first and second anchoring members.

5. The assembly of claim 1 wherein said second anchoring member comprises a unitary body.

6. The assembly of claim 1 wherein said second anchoring member is fixedly attached to said annular body.

7. The assembly of claim 1 wherein said second anchoring member is releasably attached to said annular body.

8. The assembly of claim 7 further comprising a third sealing means provided between the second anchoring member and the annular body.

9. The assembly of claim 1 further comprising a means for applying an axial expansion force along the length of said nozzle and on said one or more welds, said force extending in a direction from said vessel wall to said flange portion, said means for applying an axial expansion force comprising a stress applying device located externally of the nozzle.

10. The assembly of claim 1 wherein said annular body extends through the nozzle.

11. The assembly of claim 10 wherein said first sealing means forms a seal between the annular body and the first anchoring member.

12. The assembly of claim 11 further comprising a biasing means provided on the annular body, said biasing means urging the annular body outwardly away from the nozzle whereby said second anchoring member is urged against the inner wall of the vessel.

13. The assembly of claim 1 wherein said annular body extends from said second anchoring member and partially into said stem portion.

14. The assembly of claim 13 wherein said first sealing means forms a seal between the annular body and the stem portion.

15. A method of pressure testing one or more welds securing a nozzle to a vessel, said nozzle having a stem portion welded to an opening in the vessel wall and an opposite flange portion extending outwardly from said opening, the method comprising:
    creating a sealed annular space within the stem portion, said space being bounded by the inner surface of the stem wall and encompassing a region having said one or more welds;
    filling said annular space with a pressurising fluid;
    pressurising said annular space with said fluid and monitoring said pressure; and,
    maintaining an open channel through the nozzle during said test for communication between the interior and exterior of the vessel.

16. The method of claim 15 comprising:
    providing an assembly comprising:
        a generally annular first anchoring member for bearing against said flange portion of the nozzle , the first anchoring member having a generally central opening;
        a generally annular second anchoring member for bearing against the inner surface of said vessel wall and overlapping the opening, the second anchoring member having a generally central opening;
        an annular body having an outer diameter less than the inner diameter of said stem portion, the annular body having a lumen extending there-through;
        a first sealing means for forming a seal between said annular body and said first anchoring member or said stem portion; and, a second sealing means for forming a seal between said annular body and said second anchoring member;
    inserting said annular body generally coaxially into said stem portion;
    forming said sealed annular space between the first and second sealing means, the annular body, and said stem portion;
    forming the open channel by aligning the openings of the first and second anchoring members and the lumen of the annular body; and,
    filling and pressurising said sealed annular space.

17. The method of claim 16 wherein said filling and pressurising is conducted through one or more ports provided on the annular body.

18. The method of claim 15 further comprising applying a mechanically induced axial stress on the one or more welds during said test.

19. A weld testing assembly for testing one or more welds securing a nozzle to a vessel, said nozzle having a stem portion welded to an opening in the vessel wall and an opposite flange portion extending outward from said opening, the assembly, when in an installed condition, comprising:
   a) an anchoring sub-assembly comprising:
      a first anchoring member mountable against said flange portion of the nozzle, the first anchoring member having a generally annular shape and including a generally central opening;
      a second anchoring member mountable against the inner surface of said vessel wall and overlapping the opening, the second anchoring member having a generally annular shape and including a generally central opening;
      a vessel sealing means provided on the second anchoring member for forming a seal between the second anchoring member and the inner wall of the vessel;
      a first urging means for urging the first and second anchoring members together; and,
   b) a testing sub-assembly comprising:
      an annular body having a first end secured to the second anchoring member and a second end adapted for insertion into said nozzle stem portion, said annular body further including a lumen extending therethrough;
      a bearing member provided within the stem portion and positioned between the annular body second end and the first anchoring member,
      a stem sealing means provided between said annular body and said bearing member for sealingly engaging the inner wall of said nozzle stem portion;
      a second urging means for urging the bearing member against the second end of said annular body;
   wherein, when said assembly is in the installed condition, a sealed annular space is formed between the vessel sealing means, the stem sealing means, the annular body, and the stem portion, said space being capable of being pressurized for conducting a weld test and wherein the openings of the first and second anchoring members and the lumen of the annular body align to form an open channel through the nozzle for allowing communication between the interior and exterior of the vessel during the test.

20. The assembly of claim 19 wherein said first urging means comprises a plurality of tie rods extending between said first and second anchoring members, the tie rods being provided with a first set of nuts for urging the first and second anchoring members towards each other.

21. The assembly of claim 20 wherein said tie rods extend through said bearing member and wherein said second urging means comprises a second set of nuts provided on said tie rods, the second set of nuts being capable of being tightened against the bearing member.

22. The weld testing assembly of claim 19 further comprising:
   c) an axial stress sub-assembly comprising an axial stress applying device for positioning externally of the nozzle and adapted to apply an axial expansion force along the length of said nozzle and on said one or more welds, said axial force extending in a direction from said vessel wall to said flange portion.

23. A method of pressure testing one or more welds securing a nozzle to a vessel, said nozzle having a stem portion welded to an opening in the vessel wall and an opposite flange portion extending outwardly from said opening, the method comprising:
   providing an anchoring means extending between the vessel inner wall and the flange;
   inserting a testing tool within the stem, said testing tool being secured to the anchoring means and having a length less than the length of the stem;
   creating a sealed annular space within a localised section of the stem having said one or more welds, said sealed annular space being bounded by the inner surface of the stem wall and the outer surface of the testing tool;
   creating an open channel extending through the testing tool and the anchoring means for communication, during the test, between the interior and exterior of the vessel;
   filling said annular space with a pressurising fluid; and,
   pressurising said annular space with said fluid and monitoring said pressure.

24. The method of claim 23 further comprising applying a mechanically induced axial stress on the one or more welds during said test.

* * * * *